United States Patent
Curtis et al.

(10) Patent No.: US 8,952,149 B2
(45) Date of Patent: Feb. 10, 2015

(54) TRICYCLIC TETRAHYDROQUINOLINE ANTIBACTERIAL AGENTS

(71) Applicants: Michael Curtis, Portage, MI (US); Timothy Allan Johnson, Vicksburg, MI (US); Manjinder S. Lall, East Lyme, CT (US); Peter Laurence Toogood, Ann Arbor, MI (US); Joseph S. Warmus, Ledyard, CT (US)

(72) Inventors: Michael Curtis, Portage, MI (US); Timothy Allan Johnson, Vicksburg, MI (US); Manjinder S. Lall, East Lyme, CT (US); Peter Laurence Toogood, Ann Arbor, MI (US); Joseph S. Warmus, Ledyard, CT (US)

(73) Assignee: Zoetis LLC, Florham Park, NJ (US)

( * ) Notice: Subject to any disclaimer, the term of this patent is extended or adjusted under 35 U.S.C. 154(b) by 0 days.

(21) Appl. No.: 14/034,832

(22) Filed: Sep. 24, 2013

(65) Prior Publication Data

US 2014/0088093 A1 Mar. 27, 2014

Related U.S. Application Data

(60) Provisional application No. 61/705,709, filed on Sep. 26, 2012.

(51) Int. Cl.
*C07D 498/20* (2006.01)
*A01N 43/90* (2006.01)

(52) U.S. Cl.
CPC .............. *C07D 498/20* (2013.01); *A01N 43/90* (2013.01)
USPC .......................................................... 544/70

(58) Field of Classification Search
CPC ..................................................... C07D 498/20
USPC .............................................................. 544/70
See application file for complete search history.

(56) References Cited

FOREIGN PATENT DOCUMENTS

| WO | 2004/031195 | 4/2004 |
|----|-------------|--------|
| WO | 2006/120563 | 11/2006 |
| WO | 2007/072151 | 6/2007 |
| WO | 2009/004382 | 1/2009 |

OTHER PUBLICATIONS

Gerstenberger et al., "One-Pot Synthesis of N-Arylpyrazoles from Arylhalides", Organic Letters, 11 (10):2097-2100, 2009.
PCT International Search Report, PCT/US2013/061580, mailed Nov. 21, 2013 (3 pages).

*Primary Examiner* — Brian McDowell
(74) *Attorney, Agent, or Firm* — Martha A. Gammill

(57) ABSTRACT

Described herein are antibacterial compounds of formula I,

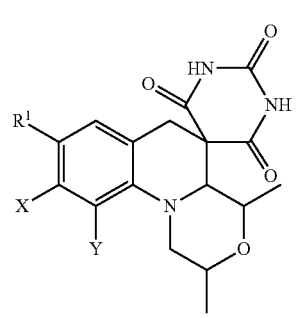

methods for making the compounds, pharmaceutical compositions containing the compounds and methods of treating bacterial infections utilizing the compounds and pharmaceutical composition.

3 Claims, No Drawings

TRICYCLIC TETRAHYDROQUINOLINE ANTIBACTERIAL AGENTS

CROSS-REFERENCE TO RELATED APPLICATIONS

This application claims benefit of priority to U.S. Provisional Application Ser. No. 61/705,709 filed Sep. 26, 2012.

FIELD OF THE INVENTION

Described herein are antibacterial compounds, their use as antibacterial agents, pharmaceutical compositions containing these compounds, and methods for their preparation.

BACKGROUND OF THE INVENTION

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. The morbidity, mortality, and financial costs of such infections pose an increasing burden for health care systems worldwide. Strategies to address these issues emphasize enhanced surveillance of drug resistance, increased monitoring and improved usage of antimicrobial drugs, professional and public education, development of new drugs, and assessment of alternative therapeutic modalities.

As a result, alternative and improved agents are needed for the treatment of bacterial infections, particularly for the treatment of infections caused by resistant strains of bacteria, e.g., penicillin-resistant, methicillin-resistant, ciprofloxacin-resistant, and/or vancomycin-resistant strains.

WO2004/031195, published Apr. 15, 2004, discloses tricyclic tetrahydroquinoline antibacterial agents.

WO2007/072151, published Jun. 28, 2007, discloses 8-pyrazinyl-S-spiropyrimidinetrione-oxazinoquinoline derivatives as antibacterial agents.

WO2009/004382, published Jan. 8, 2009, discloses 3-spiropyrimidinetrione-quinoline derivatives and their use as antibacterial agents.

WO2006/120563, published Nov. 16, 2006, discloses thiadiazol-spiropyrimidinetrione-quinoline derivatives and their use as antibacterial agents.

Brian S. Gerstenberger, Mark R. Rauckhorst and Jeremy T. Starr, "One-Pot Synthesis of N-Arylpyrazoles from Arylhalides," Organic Letters, 2009, Vol. 11, Nol. 10, 2097-2100, discloses a one-pot method for the synthesis of diversely functionalized pyrazoles.

SUMMARY OF THE INVENTION

The present invention provides a compound having formula I:

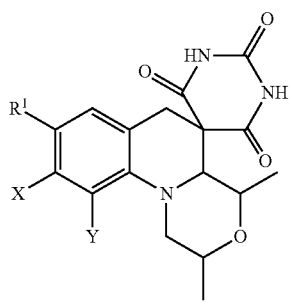

wherein:
$R^1$ is selected from the group consisting of:

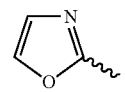  (a)

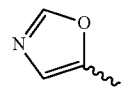  (b)

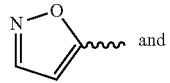 and  (c)

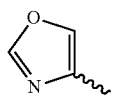  (d)

which are optionally substituted with $R^2$;
$R^2$ is $C_{1-6}$alkyl or phenyl optionally substituted with halo;
X and Y are independently H, halo or $C_{1-6}$ alkyl;
or a salt, solvate, or a hydrate thereof;
provided that when $R^1$ is moiety (b) and $R^2$ is phenyl, at least one of X and Y is halo.

The present invention further provides compounds of formula I wherein X is H or F, Y is H or F or both X and Y are H or F.

The present invention further provides compounds of formula I wherein $R^2$ is methyl or ethyl.

Forms of the compounds can include salts, such as pharmaceutically acceptable salts, solvates, hydrates or prodrugs of the described compounds. The described compounds can also be part of a pharmaceutical composition, which can additionally include a pharmaceutically acceptable carrier, diluent or excipient.

Such compounds and compositions exhibit antibacterial activity and can be used accordingly.

The present invention provides for pharmaceutical compositions comprising a compound of formula I and a pharmaceutically acceptable carrier, diluent or excipient.

The present invention provides for bacteriostatic and/or bactericidal methods comprising contacting a bacteria with a compound of formula I or a composition thereof. The present invention provides for these methods which occur in vitro or in vivo.

The present invention provides for methods of treating a bacterial infection in a mammal comprising administering an effective amount a compound of formula I or a composition thereof to the mammal. The present invention provides for these methods for preventing a bacterial infection in a mammal by administering an effective amount of the compound of formula I.

Also, the present invention provides bacteriostatic or bactericidal uses of a compound of formula I or a composition thereof comprising contacting a bacteria with a compound of formula I or a composition thereof. The present invention provides for these uses which occur in vitro or in vivo.

The present invention provides for uses of a compound of formula I or a composition thereof to treat a bacterial infection in a mammal which comprises administering an effective amount of a compound of formula I or a composition thereof to the mammal. The present invention also provides for uses of a compound of formula I or a composition thereof to prevent a bacterial infection in a mammal which comprises administering an effective amount of the compound of formula I or a composition thereof.

DETAILED DESCRIPTION

Provided herein are compounds of Formula I. When describing the compounds of Formula I, for example when naming the compounds, the ring system is numbered as follows:

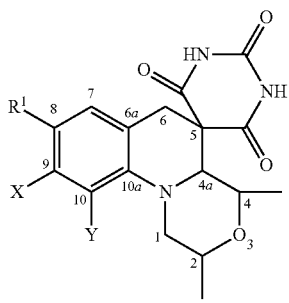

In these embodiments, ⌇⌇⌇ indicates a point of attachment.

In a subset of the compounds of Formula I, the compounds can have the stereochemistry shown in Formula Ib below:

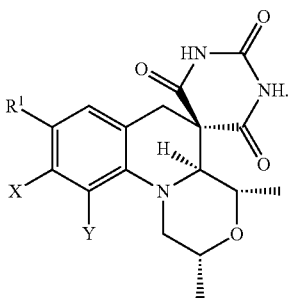

Any embodiment described herein can be combined with any other suitable embodiment described herein to provide additional embodiments. For example, where one embodiment individually or collectively describes possible groups for $R^1$, $R^2$, $R^3$, $R^4$, $R^5$, etc., and a separate embodiment describes possible $R_7$ groups, it is understood that these embodiments can be combined to provide an embodiment describing possible groups for $R^1$, $R^2$, $R^3$, $R^4$, $R^5$, etc., with the possible $R^7$ groups, etc. With respect to the above compounds, and throughout the application and claims, the following terms have the meanings defined below.

The phrase "acyl" refers to groups having a carbon double-bonded to an oxygen atom, such as in the structure —C(=O)R. Examples of R can include H, such as in aldehydes, a hydrocarbon, such as in a ketone, —$NR_8R_9$, such as in an amide, —$OR_8$ such as in a carboxylic acid or ester, —$OOCR_2$, such as in an acyl anhydride or a halo, such as in an acyl halide.

The phrase "alkenyl" refers to straight and branched chain hydrocarbons, such as those described with respect to alkyl groups described herein, that include at least one double bond existing between two carbon atoms. Examples include vinyl, —CH=C(H)(CH₃), —CH=C(CH₃)₂, —C(CH₃)=C(H)₂, —C(CH₃)=C(H)(CH₃), —C(CH₂CH₃)=CH₂, cyclohexenyl, cyclopentenyl, cyclohexadienyl, butadienyl, pentadienyl, and hexadienyl among others. An alkenyl group can optionally be substituted, for example where 1, 2, 3, 4, 5, 6, 7, 8 or more hydrogen atoms are replaced by a substituent selected from the group consisting of halogen, haloalkyl, hydroxy, thiol, cyano, and —$NR_8R_9$.

The phrase "alkyl" refers to hydrocarbon chains, for example $C_{1-6}$ chains, that do not contain heteroatoms. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, —CH(CH₂CH₃)CH(CH₃)CH(CH₃)(CH₂CH₃), and others. The phrase includes primary alkyl groups, secondary alkyl groups, and tertiary alkyl groups. Alkyl groups can be bonded to one or more carbon atom(s), oxygen atom(s), nitrogen atom(s), and/or sulfur atom(s) in the parent compound. An alkyl group can optionally be substituted, for example where 1, 2, 3, 4, 5, 6 or more hydrogen atoms are replaced by a substituent selected from the group consisting of halogen, haloalkyl, hydroxy, thiol, cyano, and —$NR_8R_9$.

The phrase "alkylene" refers to a straight or branched chain divalent hydrocarbon radical, generally having from two to ten carbon atoms.

The phrase "alkynyl" refers to straight and branched chain hydrocarbon groups, such as those described with respect to alkyl groups as described herein, except that at least one triple bond exists between two carbon atoms. Examples include —C≡C(H), —C≡C(CH₃), —C≡C(CH₂CH₃), —C(H₂)C≡C(H), —C(H)₂C≡C(CH₃), and —C(H)₂C≡C(CH₂CH₃) among others. An alkynyl group can optionally be substituted, for example where 1, 2, 3, 4, 5, 6, 7, 8 or more hydrogen atoms are replaced by a substituent selected from the group consisting of halogen, haloalkyl, hydroxy, thiol, cyano, and —$NR_8R_9$.

The phrase "aminoalkyl" refers to an alkyl group as above attached to an amino group, which can ultimately be a primary, secondary or tertiary amino group. An example of an amino alkyl group is the —$NR_8R_9$ where one or both of $R_8$ and $R_9$ is a substituted or unsubstituted $C_{1-6}$ alkyl or $R_8$ and $R_9$ together with the atom to which they are attached form a substituted or unsubstituted heterocyclic ring. Specific aminoalkyl groups include —NHCH₃, —N(CH₃)₂, —NHCH₂CH₃, —N(CH₃)CH₂CH₃, —N(CH₂CH₃)₂, —NHCH₂CH₂CH₃, —N(CH₂CH₂CH₃)₂, and the like. Additional aminoalkyl groups include:

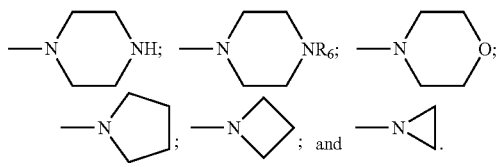

An aminoalkyl group can optionally be substituted with 1, 2, 3, 4 or more non-hydrogen substituents, for example where each substituent is independently selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)$R_6$, —C(O)O$R_6$, —S(O)$_nR_6$ and —$NR_8R_9$. These substituents may be the same or different and may be located at any position of the ring that is chemically permissible.

The phrase "aryl" refers to cyclic or polycyclic aromatic rings, generally having from 5 to 12 carbon atoms. Thus the phrase includes, but is not limited to, groups such as phenyl, biphenyl, anthracenyl, naphthenyl by way of example. The phrase "unsubstituted aryl" includes groups containing condensed rings such as naphthalene. Unsubstituted aryl groups can be bonded to one or more carbon atom(s), oxygen atom(s), nitrogen atom(s), and/or sulfur atom(s) in the parent compound. Substituted aryl groups include methoxyphenyl groups, such as para-methoxyphenyl.

Substituted aryl groups include aryl groups in which one or more aromatic carbons of the aryl group is bonded to a substituted and/or unsubstituted alkyl, alkenyl, alkynyl group or a heteroatom containing group as described herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl, and hydroxyphenyl among others. An aryl moiety can optionally be substituted with 1, 2, 3, 4 or more non-hydrogen substituents, for example where each substituent is independently selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$. These substituents may be the same or different and may be located at any position of the ring that is chemically permissible.

The phrase "cycloalkyl" refers to cyclic hydrocarbon chains, generally having from 3 to 12 carbon atoms, and includes cyclic alkyl groups such as cyclopropyl, cyclobutyl, cyclopentyl, cyclohexyl, cycloheptyl, and cyclooctyl and such rings substituted with straight and branched chain alkyl groups as described herein. The phrase also includes polycyclic alkyl groups such as, but not limited to, adamantly, norbornyl, and bicyclo[2.2.2]octyl and such rings substituted with straight and branched chain alkyl groups as described herein. Cycloalkyl groups can be saturated or unsaturated and can be bonded to one or more carbon atom(s), oxygen atom(s), nitrogen atom(s), and/or sulfur atom(s) in the parent compound. A cycloalkyl group can be optionally substituted, for example where 1, 2, 3, 4 or more hydrogen atoms are replaced by a substituent selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$.

Ethers, as used herein, generically encompass monoethers, polyethers, straight chain ethers, branched ethers and cyclic ethers. Straight chain ethers can have the structure —[(CH$_2$)$_p$O(CH$_2$)$_p$]$_q$CH$_3$ where each p is independently 0, 1, 2, 3, 4, 5 or 6 and q is 1, 2, 3, 4, 5 or 6. Branched ethers can have the formula —[(CV$_2$)$_p$O(CV$_2$)$_p$]$_q$CH$_3$ where each V is independently H or another —[(CV$_2$)$_p$O(CV$_2$)$_p$]$_q$CH$_3$ group. Cyclic ethers can have the formula

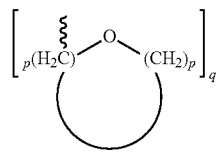

where p and q are as above and ∿ indicates a point of attachment. Specifically, as ether compounds, there are -dimethyl ether, -methyl ethyl ether, -methoxy ethyl ether, -diethyl ether, -methyl t-butyl ether, -methyl cellosolve, -ethylene glycol dimethyl ether, -diethylene glycol dimethyl ether, -triethylene glycol dimethyl ether, -tetraethylene glycol dimethyl ether, -tetrahydrofuran, -1,4-dioxane, and the like.

The phrase "halo" refers to fluorine, chlorine, bromine or iodine.

The phrase "haloalkyl" refers to an alkyl group in which at least one, for example 1, 2, 3, 4, 5 or more, hydrogen atom(s) is/are replaced with a halogen. Examples of suitable haloalkyls include chloromethyl, difluoromethyl, trifluoromethyl, 1-fluoro-2-chloro-ethyl, 5-fluoro-hexyl, 3-difluoro-isopropyl, 3-chloro-isobutyl, etc.

The phrases "heterocyclyl" or "heterocyclic ring" refers to aromatic, nonaromatic, saturated and unsaturated ring compounds including monocyclic, bicyclic, and polycyclic ring compounds, including fused, bridged, or spiro systems, such as, but not limited to, quinuclidyl, containing 1, 2, 3 or more ring members of which one or more is a heteroatom such as, but not limited to, N, O, P and S. Unsubstituted heterocyclyl groups include condensed heterocyclic rings such as benzimidazolyl. Examples of heterocyclyl groups include: unsaturated 3- to 8-membered rings containing 1 to 4 nitrogen atoms such as, but not limited to pyrrolyl, pyrrolinyl, imidazolyl, imidazolidinyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3- to 8-membered rings containing 1 to 4 nitrogen atoms such as, but not limited to, pyrrolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; saturated 3- to 8-membered rings containing 1 to 3 oxygen atoms such as, but not limited to, tetrahydrofuran; unsaturated 3- to 8-membered rings containing 1 to 2 oxygen atoms and 1 to 3 nitrogen atoms such as, but not limited to, oxazolyl, isoxazolyl, oxadiazolyl (e.g., 1,2,4-oxadiazolyl, 1,3,4-oxadiazolyl, 1,2,5-oxadiazolyl, etc.); saturated 3- to 8-membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3- to 8-membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3- to 8-membered rings containing 1 to 2 sulfur atoms and 1 to 3 nitrogen atoms such as, but not limited to, thiazolodinyl; saturated and unsaturated 3- to 8-membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g., 2H-1,4-benzothiazinyl, etc.), dihydrobenzothiazinyl (e.g., 2H-3,4-dihydrobenzothiazinyl, etc.), unsaturated 3- to 8-membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3- to 8-membered rings containing an oxygen atom and 1 to 2 sulfur atoms such as; but not limited to, dihydrooxathiinyl; saturated 3- to 8-membered rings containing 1 to 2 oxygen atoms, and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl groups also include those described herein in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Heterocyclyl groups can contain 5 or 6 ring members. Examples of heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

A heterocyclyl group can be optionally substituted, for example where 1, 2, 3, 4 or more hydrogen atoms are replaced by a substituent selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$. Examples of "substituted heterocyclyl" rings include 2-methylbenzimidazolyl, 5-methylbenzimidazolyl, 5-chlorobenzthiazolyl, 1-methylpiperazinyl, and 2-chloropyridyl among others. Any nitrogen atom within a heterocyclic ring can optionally be substituted with $C_{1-6}$ alkyl, if chemically permissible.

Heterocyclyl groups include heteroaryl groups as a subgroup. The phrase "heteroaryl" refers to a monovalent aromatic ring radical, generally having 5 to 10 ring atoms, containing 1, 2, 3, or more heteroatoms independently selected from S, O, or N. The term heteroaryl also includes bicyclic groups in which the heteroaryl ring is fused to a benzene ring, heterocyclic ring, a cycloalkyl ring, or another heteroaryl ring. Examples of heteroaryl include 7-benzimidazolyl, benzo[b]thienyl, benzofuryl, benzothiazolyl, benzothiophenyl, 2-, 4-, 5-, 6-, or 7-benzoxazolyl, furanyl, furyl, imidazolyl, indolyl, indazolyl, isoquinolinyl, isothiazolyl, isoxazolyl, oxadiazolyl, oxazolyl, purinyl, pyrazinyl, pyrazolyl, pyridazinyl, pyridinyl, pyrimidinyl, pyrrolyl, quinolinyl, tetrazolyl, thiadiazolyl, thiazolyl, thienyl, thiophenyl, triazolyl and the like. Heteroaryl rings can also be optionally fused to one or more of another heterocyclic ring(s), heteroaryl ring(s), aryl ring(s), cycloalkenyl ring(s), or cycloalkyl rings. A heteroaryl group can be optionally substituted, for example where 1, 2, 3, 4 or more hydrogen atoms are replaced by a substituent selected from the group consisting of halogen, cyano, hydroxy, $C_{1-6}$ alkyl, $C_{1-6}$ alkoxy, $C_{1-2}$ alkyl substituted with one or more halogens, $C_{1-2}$ alkoxy substituted with one or more halogens, —C(O)R$_6$, —C(O)OR$_6$, —S(O)$_n$R$_6$ and —NR$_8$R$_9$.

The phrase "heterocyclyloxy" refers to a group in which an oxygen atom is bound to a ring atom of a heterocyclyl group as described herein.

"Pharmaceutically acceptable" means suitable for use in mammals. A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid. Examples of pharmaceutically acceptable salts are described in Berge, S. M., et al., "Pharmaceutical Salts," Journal of Pharmaceutical Science, 1977; 66:1-19.

A "prodrug" is a compound that can be transformed in vivo into an active therapeutic compound, such as a compound described herein. Transformation of the prodrug compound can be accomplished chemically, enzymatically, or by action with other endogenous materials, e.g., amino acids, peptides and proteins. Prodrugs are discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987. Examples of prodrugs can include esters and amides of polar groups, such as carboxylate groups.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y. (3rd Edition, 1999), which can be added or removed using the procedures set forth therein. Examples of protected hydroxyl groups include silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include amides such as, formamide, acetamide, trifluoroacetamide, and benzamide; imides, such as phthalimide, and dithiosuccinimide; and others. Examples of protected sulfhydryl groups include thioethers such as S-benzyl thioether, and S-4-picolyl thioether; substituted S-methyl derivatives such as hemithio, dithio and aminothio acetals; and others.

A "salt" refers to all salt forms of a compound, including salts suitable for use in industrial processes, such as the preparation of the compound, and pharmaceutically acceptable salts.

"Substituted" refers to a group in which one or more bonds to a hydrogen atom contained therein are replaced by a bond to non-hydrogen atom. In some instances the bond will also be replaced by non-carbon atoms such as, but not limited to: a halogen atom such as F, Cl, Br, and I; a nitrogen atom in groups such as amines, amides, alkylamines, dialkylamines, arylamines, alkylarylamines, diarylamines, heterocyclylamine, (alkyl)(heterocyclyl)amine, (aryl)(heterocyclyl) amine, or diheterocyclylamine groups, isonitrile, N-oxides, imides, and enamines; an oxygen atom in groups such as hydroxyl groups, alkoxy groups, aryloxy groups, ester groups, and heterocyclyloxy groups; a silicon atom in groups such as in trialkylsilyl groups, dialkylarylsilyl groups, alkyldiarylsilyl groups, and triarylsilyl groups; a sulfur atom in groups such as thiol groups, alkyl and aryl sulfide groups, sulfone groups, sulfonyl groups, and sulfoxide groups; and other heteroatoms in various other groups. Substituted alkyl groups and substituted cycloalkyl groups also include groups in which one or more bonds to one or more carbon or hydrogen atoms are replaced by a bond to a heteroatom such as oxygen in carbonyl, carboxyl, and ether groups; nitrogen in groups such as imines, oximes and hydrazones. Substituted cycloalkyl, substituted aryl, substituted heterocyclyl and substituted heteroaryl also include rings and fused ring systems which can be substituted with alkyl groups as described herein. Substituted arylalkyl groups can be substituted on the aryl group, on the alkyl group, or on both the aryl and alkyl groups. All groups included herein, such as alkyl, alkenyl, alkylene, alkynyl, aryl, heterocyclyl, heterocyclyloxy, and the like, can be substituted. Representative examples of substituents for substitution include one or more, for example one, two or three, groups independently selected from halogen, —OH, —$C_{1-6}$ alkyl, $C_{1-6}$ alkoxy, trifluoromethoxy, —S(O)$_n$$C_{1-6}$ alkyl, amino, haloalkyl, thiol, cyano, —OR$_{10}$ and —NR$_8$R$_9$, and trifluoromethyl.

"Treating" means an alleviation of symptoms associated with an infection, halt of further progression or worsening of those symptoms, or prevention or prophylaxis of the infection. Treatment can also include administering the pharmaceutical formulations of the present invention in combination with other therapies. For example, the compounds and pharmaceutical formulations of the present invention can be administered before, during, or after surgical procedure and/or radiation therapy. The compounds of the invention can also be administered in conjunction with other antibacterial drugs.

In some instances, compounds described herein can be provided ex vivo or produced in vivo, for example where a prodrug of a compound is administered.

Generally, reference to a certain element such as hydrogen or H is meant to include all isotopes of that element. For example, if an R group is defined to include hydrogen or H, it also includes deuterium and tritium. Chemical formulas throughout are designated with capital Roman numerals for simplified identification. Roman numerals used in conjunction with a small letter, for example 1a, indicate that the structure set forth is an enantiomer of the compound identified by the Roman numeral. Roman numerals used in conjunction with a prime symbol, for example III', indicate that the structure set forth can have one or more protected groups which are included in atoms groups identified with the prime symbol, for example where O' indicates an oxygen atom or a protected aldehyde group.

General Synthesis of Compounds. The described compounds can be made according to the general synthetic schemes, as described in U.S. Pat. Nos. 7,557,100 and 7,605,157, which are hereby incorporated by reference herein.

The compounds described herein can also be synthesized by appropriately modifying the protocols set forth in WO 2004/031195.

Certain compounds described herein are also useful as intermediates for preparing other described compounds and such intermediates are included within the scope of the present invention.

Specific compounds are described throughout with particular reference to the Examples, in which compounds starting with "rel-" or denoted by ± are racemic compounds.

Also provided are compositions that can be prepared by mixing one or more compounds described herein, or pharmaceutically acceptable salts or tautomers thereof, with pharmaceutically acceptable carriers, excipients, binders, diluents or the like, to treat or ameliorate a variety of bacterial infections. A therapeutically effective dose or amount refers to that amount of one or more compounds described herein sufficient to result in amelioration of symptoms of the infection. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments can be added for identification. Tablets and pills can be further treated with suitable coating materials known in the art.

Liquid dosage forms for oral administration can be in the form of pharmaceutically acceptable emulsions, syrups, elixirs, suspensions, slurries and solutions, which can contain an inactive diluent, such as water. Pharmaceutical formulations can be prepared as liquid suspensions or solutions using a sterile liquid, such as, but not limited to, an oil, water, an alcohol, and combinations of these. Pharmaceutically suitable surfactants, suspending agents, emulsifying agents, can be added for oral or parenteral administration.

As noted above, suspensions can include oils. Such oils include peanut oil, sesame oil, cottonseed oil, corn oil, olive oil and mixtures of oils. Suspension preparation can also contain esters of fatty acids such as ethyl oleate, isopropyl myristate, fatty acid glycerides and acetylated fatty acid glycerides. Suspension formulations can include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water can also be used in suspension formulations.

For nasal administration, the pharmaceutical formulations can be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation can include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Generally, the oil or fatty acid is non-volatile, including natural or synthetic oils, fatty acids, mono-, di- or tri-glycerides.

For injection, the pharmaceutical formulation can be a powder suitable for reconstitution with an appropriate solution as described above. Examples of these include freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

For rectal administration, the pharmaceutical formulations can be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils can also be employed in the preparation of formulations of the soft gelatin type and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences", Mack Pub. Co., New Jersey (1991).

The formulations of the invention can be designed to be short-acting, fast-releasing, long-acting, and sustained-releasing. Thus, the pharmaceutical formulations can also be formulated for controlled release or for slow release.

The instant compositions can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The compositions can contain, for example, from about 0.1% by weight, to about 90% or more by weight, of the active material, depending on the method of administration. Where the compositions comprise dosage units, each unit can contain, for example, from about 5 to 500 mg or more of the active ingredient. The dosage as employed for adult human treatment can range, for example, from about 10 to 3000 mg per day, depending on the route and frequency of administration.

Specific dosages can be adjusted depending on conditions of infection, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 0.1 mg/kg/day to about 500 mg/kg/day in single or in divided doses. Typically, dosages for humans can range from about 10 mg to about 3000 mg per day, in a single or multiple doses.

A therapeutically effective dose or amount can vary depending upon the route of administration and dosage form. Some compositions of the instant invention provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

In one embodiment, the invention provides methods of treating or preventing a bacterial infection in a subject, such as a mammal, e.g., a human or non-human mammal, comprising administering an effective amount of one or more compounds described herein to the subject. Suitable subjects that can be treated include domestic or wild animals, companion animals, such as dogs, cats and the like; livestock, including horses, cows and other ruminants, pigs, poultry, rabbits and the like; primates, for example monkeys, such as rhesus monkeys and cynomolgus (also known as crab-eating or long-tailed) monkeys, marmosets, tamarinds, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier. The compounds described herein can be used for the treatment or prevention of infectious disorders caused by a variety of bacterial organisms, including infections by pathogenic bacterial species. Examples include Gram positive and Gram negative aerobic and anaerobic bacteria, such as Staphylococci, e.g., *S. aureus*; Enterococci, e.g., *E. faecalis*; Streptococci, e.g., *S. pyogenes* and *S. pneumoniae; Escherichia* species, e.g., *E. coli*, including enterotoxigenic, enteropathogenic, enteroinvasive, enterohemorrhagic and enteroaggregative *E. coli* strains; *Haemophilus*, e.g., *H. influenza; Moraxella*, e.g., *M. catarrhalis*. Other examples include *Mycobacteria*, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum; Corynebacteria*, e.g., *C. diphtheriae; Vibrio* species, e.g., *V. cholerae; Campylobacter* species, e.g., *C. jejuni; Helicobacter* species, e.g., *H. pylori; Pseudomonas* species, e.g., *P. aeruginosa; Legionella* species, e.g., *L. pneumophila; Treponema* species, e.g., *T. pallidum; Borrelia* species, e.g., *B. burgdorferi; Listeria* species, e.g., *L. monocytogenes; Bacillus* species, e.g., *B. cereus; Bordatella* species, e.g., *B. pertussis; Clostridium* species, e.g., *C. perfringens, C. tetani, C. difficile* and *C. botulinum; Neisseria* species, e.g., *N. meningitidis* and *N. gonorrhoeae; Chlamydia* species, e.g., *C. psit-*

*taci, C. pneumoniae* and *C. trachomatis; Rickettsia* species, e.g., *R. rickettsii* and *R. prowazekii; Shigella* species, e.g., *S. sonnei; Salmonella* species, e.g., *S. typhimurium; Yersinia* species, e.g., *Y. enterocolitica* and *Y. pseudotuberculosis; Klebsiella* species, e.g., *K. pneumoniae*; and *Mycoplasma*, e.g., *M. pneumoniae*.

Infections that can be treated with the described compounds include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. These infections can be treated in hospital or community settings via various routes of administration as described herein.

The compounds or compositions described herein can also be used prophylactically. Accordingly, one or more of the present compounds or compositions can be administered to an individual deemed to be at risk for developing a microbial infection. Individuals at risk for developing a microbial infection include individuals who have been exposed to a particular microorganism, such as a pathogenic bacterial species; individuals having a compromised immune system, such as individuals suffering from an immunodeficiency disease or taking immunocompromising medication; and individuals having a history of repeated or chronic infection, such as children who have repeated infections of the middle ear.

Another embodiment provides a method of killing or preventing the growth of bacteria that includes contacting bacteria with either a non-therapeutic amount or a therapeutically effective amount of one or more of the present compounds. Such methods can occur in vivo or in vitro. In vitro contact can involve a screening assay to determine the efficacy of the one or more compounds against selected bacteria at various amounts or concentrations. In vivo contact with a therapeutically effective amount of the one or more compounds can involve treatment or prophylaxis of a bacterial infection in the animal in which the contact occurs. The effect of the one or more compounds on the bacteria and/or host animal can also be determined or measured.

Included within the scope of the invention are all isomers (e.g. stereoisomers, diastereoisomers, epimers, geometrical isomers) of the compounds described herein as well as any wholly or partially equilibrated mixtures thereof (e.g. racemic or optically active mixtures). The present invention also covers the individual isomers of the compounds represented by the formulas herein as mixtures with isomers thereof in which one or more chiral centers are inverted.

Stereoisomeric mixtures, e.g., mixtures of diastereomers, can be separated into their corresponding isomers in a known manner by means of suitable separation methods. Diastereomeric mixtures for example can be separated into their individual diastereomers by means of fraction crystallization, chromatography, solvent distribution, and similar procedures. This separation can take place either at the level of one of the starting compounds or in a compound of formula I itself. Enantiomers can be separated through the formation of diastereomeric salts, for example by salt formation with an enantiomerically pure chiral acid, or by means of chromatography, for example by HPLC, using chiral chromatographic media.

It is understood that the compounds described herein can exhibit the phenomenon of tautomerism. As the chemical structures sometimes only represent one of the possible tautomeric forms, it should be understood that the invention encompasses any tautomeric form of the represented structure.

In addition, the compounds described herein can exist in unsolvated as well as solvated forms with pharmaceutically acceptable solvents such as water, ethanol, and the like. In general, the solvated forms are considered equivalent to the unsolvated forms for the purposes of the present invention.

Relative stereochemistry for racemic compounds was assigned based on the R or S designation of the structures as set forth in the structures above.

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_1$-$C_6$, includes the subranges $C_2$-$C_6$, $C_3$-$C_6$, $C_3$-$C_5$, $C_4$-$C_6$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

All references disclosed herein are specifically incorporated herein by reference thereto.

While specific embodiments have been illustrated and described, it should be understood that these embodiments do not limit the scope of the invention and that changes and modifications can be made in accordance with ordinary skill in the art without departing from the invention in its broader aspects as defined in the following claims. Reference to a "step" in the application is used for convenience purposes only and does not categorize, define or limit the invention as set forth herein.

EXAMPLES
Example 1
Preparation of (2R,4S,4aS)-10-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione
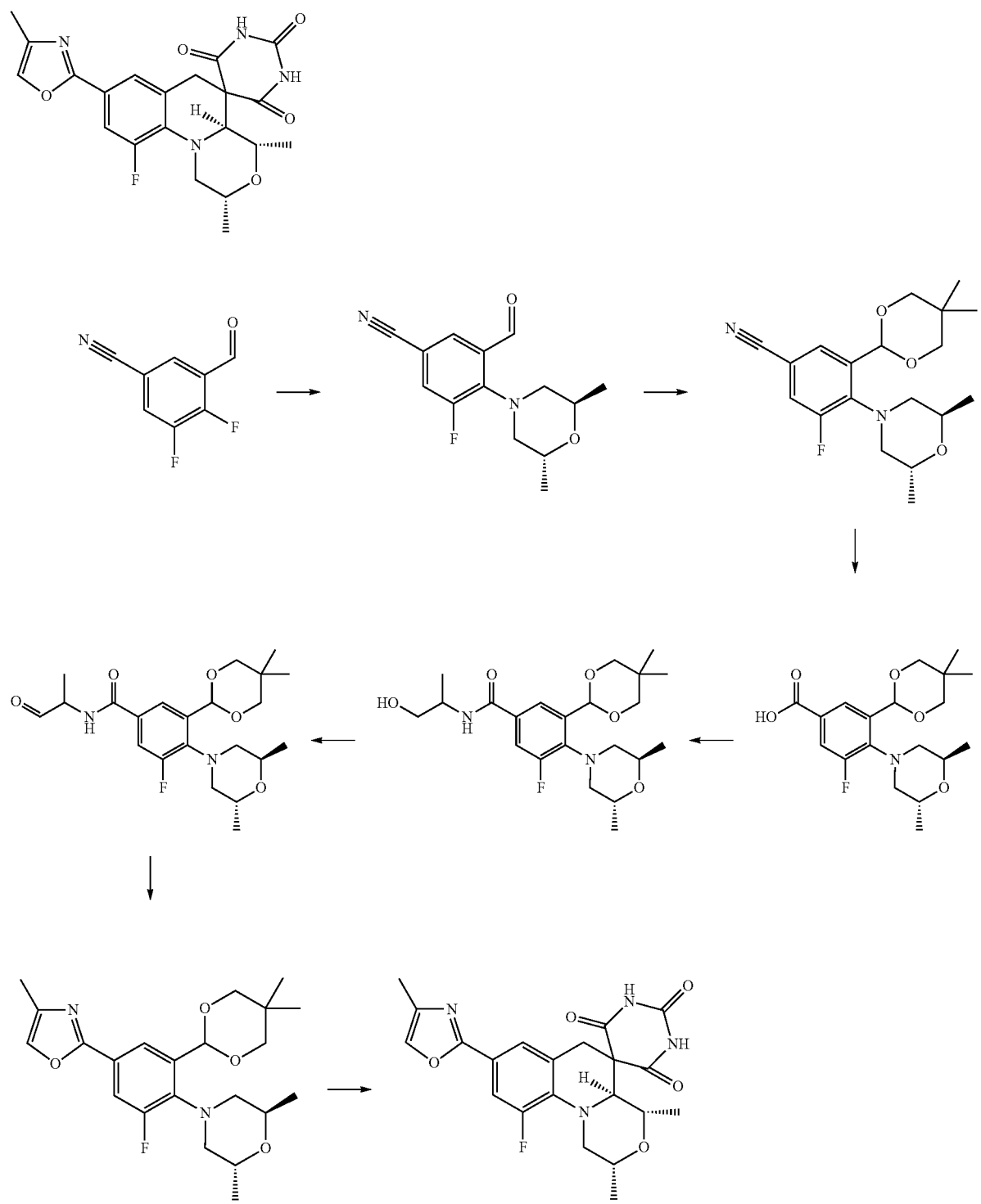

Step 1: Preparation of 4-((2R,6R)-2,6-dimethylmorpholino)-3-fluoro-5-formylbenzonitrile

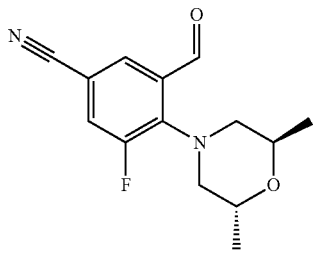 [SMILES: C[C@@H]1CN(c2c(F)cc(C#N)cc2C=O)C[C@@H](C)O1]

(2R,6R)-2,6-dimethylmorpholine (8.0 g, 70.0 mmol) followed by triethylamine (13.7 mL, 98.0 mmol) is added slowly to a solution of commercially available 3,4-difluoro-5-formylbenzonitrile (11.1 g, 66.7 mmol) in acetonitrile (500 mL) at room temperature. The mixture is warmed to 80° C. for 16 hours. After allowing to cool to room temperature, water (500 mL) is added and the mixture extracted twice with ethylacetate (250 mL). The combined organics were washed with brine, dried over sodium sulfate, filtered and evaporated to give the title compound (18.1 g): LCMS (M+H) 262.3.

Step 2: Preparation of 3-(5,5-dimethyl-1,3-dioxan-2-yl)-4-((2R,6R)-2,6-dimethylmorpholino)-5-fluorobenzonitrile

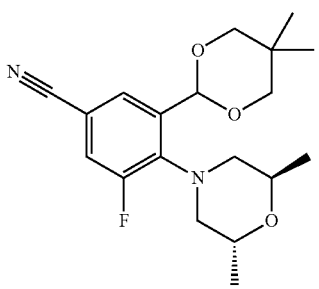 [SMILES: C[C@@H]1CN(c2c(F)cc(C#N)cc2C2OCC(C)(C)CO2)C[C@@H](C)O1]

The product of step 1—Example 1 (12.0 g, 45.7 mmol) is dissolved in toluene (100 mL) and 2,2-bis(hydroxymethyl) propane is added, followed by 4-toluenesulfonic acid (788 mg, 4.58 mmol). The reaction mixture is heated to reflux with a Dean-Stark trap for 2 hours. After cooling to room temperature saturated sodium hydrogen carbonate (150 mL) is added and the mixture extracted twice with ethylacetate (150 mL). The combined organics are dried over magnesium sulfate, filtered and evaporated to give the title compound (15.0 g): LCMS (M+H) 348.2.

Step 3: Preparation of 3-(5,5-dimethyl-1,3-dioxan-2-yl)-4-((2R,6R)-2,6-dimethylmorpholino)-5-fluorobenzoic acid

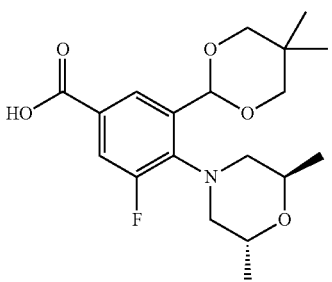

To a stirred solution of the product of step 2—Example 1 (10.5 g, 30.1 mmol) in ethanol (75 mL) is added 5M sodium hydroxide (60.3 mL, 301 mmol). The reaction mixture is heated to 60° C. for 6 hours. The reaction is cooled to room temperature and concentrated under vacuum. Remaining aqueous solution is acidified to pH=2 using aqueous sodium bisulfate. The resulting precipitate is filtered and dried under vacuum at 40° C. for 24 hours. The crude material is dissolved in ethylacetate (350 mL), washed with water (2×100 mL), dried (Na$_2$SO$_4$), and concentrated under reduced pressure to give the title compound (7.68 g): LCMS (M−H) 368.3.

Step 4: Preparation of 3-(5,5-dimethyl-1,3-dioxan-2-yl)-4-((2R,6R)-2,6-dimethylmorpholino)-5-fluoro-N-(1-hydroxypropan-2-yl)benzamide

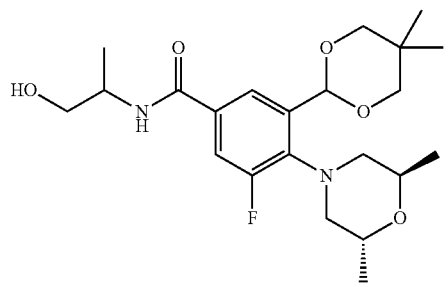 [SMILES: CC(CO)NC(=O)c1cc(F)c(N2C[C@@H](C)O[C@H](C)C2)c(C2OCC(C)(C)CO2)c1]

To a solution of the product of step 3—Example 1 (1.3 g, 3.5 mmol) in DMF (10 mL) is added O-(7-azabenzotriazol-1-yl)-N,N,N',N'-tetramethyluronium hexafluorophosphate (HATU) (1.6 g, 4.2 mmol) and triethylamine (0.59 mL, 4.2 mmol). The reaction is stirred at room temperature for 15 minutes then treated with DL-alaminol (266 mg, 3.5 mmol). The reaction is stirred at room temperature for 18 hours, then diluted with ethylacetate (75 mL) and washed twice with 1M NaOH (50 mL), dried and concentrated under vacuum. The crude material is chromatographed using a gradient of 70:30 hexane:ethylacetate to 20:80 hexane:ethylacetate to give the title compound (1.13 g): LCMS (M+H) 421.3.

Step 5: Preparation of 3-(5,5-dimethyl-1,3-dioxan-2-yl)-4-((2R,6R)-2,6-dimethylmorpholino)-5-fluoro-N-(1-oxopropan-2-yl)benzamide

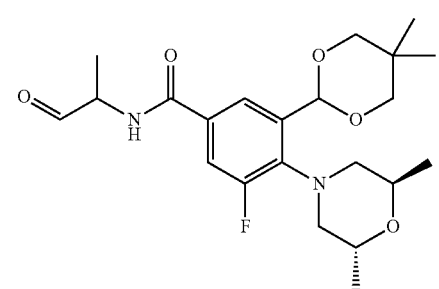

To a solution of the product of step 4—Example 1 (1.10 g, 2.59 mmol) in DMSO (10 mL) is added 2-iodoxybenzoic acid (3.22 g, 5.2 mmol). The reaction is stirred at room temperature for 18 hours. The reaction is diluted with ethylacetate (75 mL) and washed twice with saturated NaHCO$_3$ (50 mL), dried and concentrated under vacuum to give the title compound (456 mg): LCMS (M+H) 405.3.

Step 6: Preparation of (2R,6R)-4-(2-(5,5-dimethyl-1,3-dioxan-2-yl)-6-fluoro-4-(4-methyloxazol-2-yl)phenyl)-2,6-dimethylmorpholine

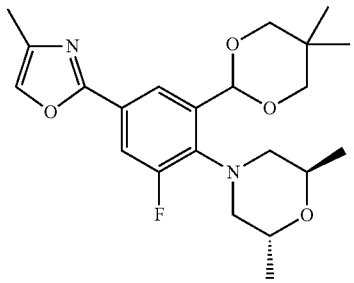

To a solution of the product of step 5—Example 1 (435 mg, 1.03 mmol) in CH$_2$Cl$_2$ (5 mL) is added triphenylphosphine (810 mg, 3.09 mmol), hexachloroethane (731 mg, 3.09 mmol), and triethylamine (0.86 mL, 6.18 mmol). The reaction is stirred at room temperature for 18 hours. 1,8-Diazabicycloundec-7-ene (1.5 g, 10 mmol) is added and reaction heated to 40° C. for 3 hours. Reaction is diluted with CH$_2$Cl$_2$ (75 mL) washed with water (75 mL), dried (Na$_2$SO$_4$) and concentrated under vacuum to give the title compound (330 mg): LCMS (M+H) 404.2.

Step 7: Preparation of (2R,4S,4aS)-10-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione

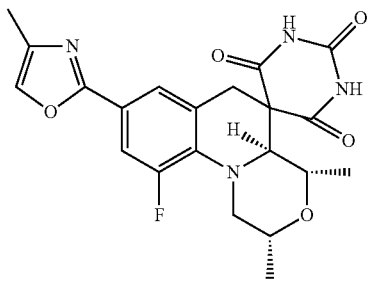

To a solution of the product of Step 6—Example 1 (0.32 g, 0.79 mmol) in 3:2 acetic acid:water (15 mL) is added barbituric acid (122 mg, 0.95 mmol) and the contents heated to 110° C. for 2 hours. The mixture is cooled to 0° C., concentrated under vacuum, azeotroped with toluene (3×10 mL). The crude material is purified by flash chromatography eluting from 80:20 hexanes:ethylacetate to 50:50 hexanes:ethylacetate to give title compound as a single enantiomer (0.071 g): $^1$HNMR (400 MHz, DMSO-d$_6$): 0.87 (d, 3H), 1.08 (d, (3H), 2.07 (s, 3H), 2.98-2.88 (m, 2H), 3.52 (d, 1H), 3.61 (m, 1H), 3.72 (m, 1H), 3.83 (d, 1H), 4.03 (d, 1H), 7.35 (s, 1H), 7.42 (d, 1H), 7.75 (s, 1H); LCMS (M+H) 428.2.

Example 2

Preparation of (2R,4S,4aS)-9,10-difluoro-2,4-dimethyl-8-(3-methylisoxazol-5-yl)-2,4,4a,6-tetrahydro-1H,1'H-spiro[[1,4]oxazino[4,3-a]quinoline-5,5'-pyrimidine]-2',4',6'(3'H)-trione

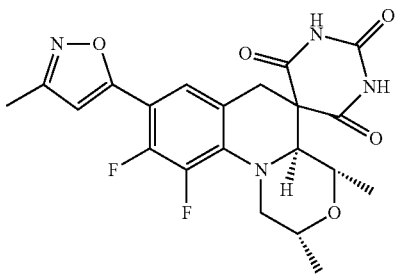

Step 1: Preparation of tert-butyl (2-(5-(5,5-dimethyl-1,3-dioxan-2-yl)-4-(2R,6R)-2,6-dimethylmorpholino)-2,3-difluorophenyl)-2-oxoethyl)carbamate

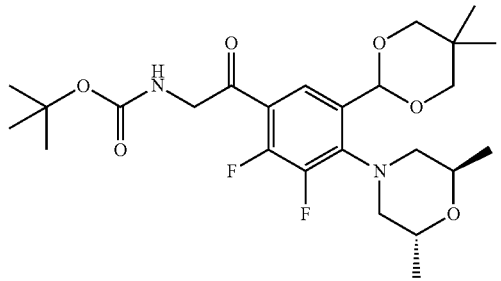 [SMILES: C[C@@H]1CN(c2c(C3OCC(C)(C)CO3)cc(C(=O)CNC(=O)OC(C)(C)C)c(F)c2F)C[C@@H](C)O1]

To a solution of (2R,6R)-4-(4-bromo-6-(5,5-dimethyl-1,3-dioxan-2-yl)-2,3-difluorophenyl)-2,6-dimethylmorpholine is (previously reported in Organic Letters, 2009, Vol. 11, No. 10, 2097-2100, 2098, 420 mg, 1.0 equiv, 1.0 mmol) and Boc-Gly-N(OMe)-Me (436 mg, 2.0 mmol, 2.0 equiv) in tetrahydrofuran (5 mL) is added iso-propylmagnesium chloride (1.5 mL, 3.0 mmol, 3.0 equiv). The reaction is heated to 100° C. for 5 mins and then cooled to room temperature. The reaction is quenched with saturated aqueous NH$_4$Cl (5 mL) and extracted with ethyl acetate (3×5 mL). The organic layer is dried with sodium sulfate, filtered through celite, and concentrated in vacuo to give the crude material, which is purified via analogix column (15-24 g, 10% ethyl acetate in heptane 1 min then to 30% ethyl acetate over 20 mins) peak 1 at 4 mins to give the title compound (272 mg): $^1$H NMR (400 MHz, DMSO-d$_6$) 0.61-0.80 (m, 3H), 1.07-1.23 (m, 9H), 1.35 (s, 9H), 2.79 (dd, 2H), 3.19 (d, 2H), 3.52-3.74 (m, 4H), 4.01-4.24 (dd, 2H), 5.69 (s, 1H), 7.11 (t, 1H), 7.78 (d, 1H).

Step 2: Preparation of 2-amino-1-(5-(5,5-dimethyl-1,3-dioxan-2-yl)-4-((2R,6R)-2,6-dimethylmorpholino)-2,3-difluorophenyl)ethanone

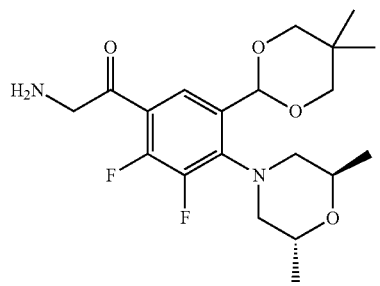 [SMILES: C[C@@H]1CN(c2c(C3OCC(C)(C)CO3)cc(C(=O)CN)c(F)c2F)C[C@@H](C)O1]

A flask with the product of Step 1—Example 2 (270 mg, 0.542 mmol, 1.0 equiv) is cooled to 0° C. An ice cooled solution of 80% aqueous trifluoroacetic acid (5 mL) is added. The reaction is stirred at 0° C. for 35 minutes. The reaction is quenched with saturated sodium bicarbonate and extracted with dichloromethane/iso-propylalcohol (1:1, 20 mL) to give the title compound (196 mg): LCMS (M+H) 398.3.

Step 3: Preparation of (2R,6R)-4-(6-(5,5-dimethyl-1,3-dioxan-2-yl)-2,3-difluoro-4-(3-methylisoxazol-5-yl)phenyl)-2,6-dimethylmorpholine

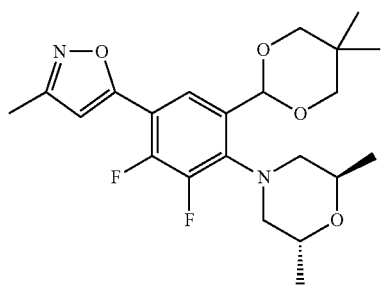

To a solution of the product of Step 2—Example 2 (1.11 g, 2.64 mmols) in triethyl orthoacetate (10 mL, 55 mmol, 21.0 equiv) is added para-toluenesulfonic acid (14 mg, 0.08 mmol, 0.03 equiv). The reaction is heated to reflux for 16 hours (165° C.). The solvent is removed under reduced pressure and the crude compound purified by analogix (25-40 g, 10% ethyl acetate in heptane 2 mins then to 20% over 20 mins) to give the title compound (490 mg) $^1$H NMR (400 MHz, DMSO-d6) 0.75 (s, 3H), 1.17-1.22 (m, 9H), 2.50 (s, 3H), 2.73 (dd, 2H), 3.03-3.20 (m, 2H), 3.59-3.73 (m, 2H), 3.95-4.10 (m, 2H), 5.78 (s, 1H), 7.37-7.41 (m, 1H), 7.64 (dd, 1H).

Step 4: Preparation of (2R,4S,4aS)-9,10-difluoro-2,4-dimethyl-8-(3-methylisoxazol-5-yl)-2,4,4a,6-tetrahydro-1H,1'H-spiro[[1,4]oxazino[4,3-a]quinoline-5,5'-pyrimidine]-2',4',6'(3'H)-trione

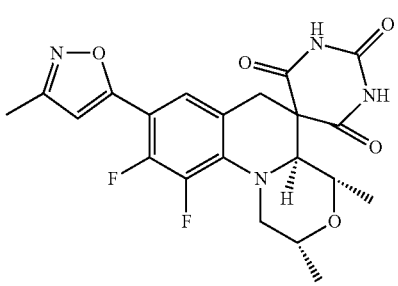

Using the same procedure as Step 7—Example 1 and making non-critical variations the title compound is obtained as a single enantiomer (2.51 g): $^1$H NMR DMSO-d$_6$: 0.86 (3H, d), 1.09 (3H, d), 2.24 (3H, s), 2.87 (1H, s), 2.94-3.09 (1H, m), 3.53 (1H, d), 3.61 (1H, dd), 3.68-3.78 (1H, m), 3.85 (1H, d), 4.04 (1H, dd), 6.50 (1H, d), 7.25 (1H, d), 11.50 (1H, br s), 11.81 (1H, br s); LCMS (M+H) 446.1.

Example 3

Preparation of (2R,4S,4aS)-10-fluoro-2,4-dimethyl-8-(oxazol-2-yl)-2,4,4a,6-tetrahydro-1H,1'H-spiro[[1,4]oxazino[4,3-a]quinoline-5,5'-pyrimidine]-2',4',6'(3'H)-trione

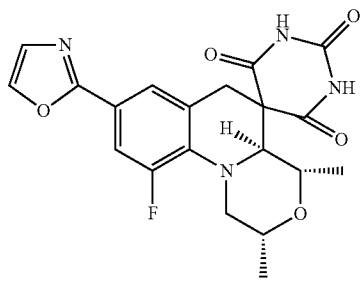

Step 1: Preparation of 3-(5,5-dimethyl-1,3-dioxan-2-yl)-4-((2R,6R)-2,6-dimethylmorpholino)-5-fluoro-N-(2-hydroxyethyl)benzamide

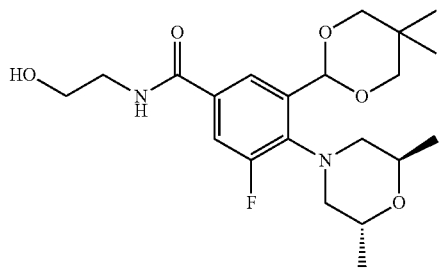 [SMILES: C[C@@H]1CN(c2c(F)cc(C(=O)NCCO)cc2C2OCC(C)(C)CO2)C[C@@H](C)O1]

To a solution of the product of Step 3—Example 1 (1.3 g, 3.5 mmol) in DMF (10 mL) is added O-(7-azabenzotriazol-1-yl)-N,N,N',N'-tetramethyluronium hexafluorophosphate (HATU) (1.6 g, 4.3 mmol) and triethylamine (0.59 mL, 4.2 mmol). The reaction is stirred at room temperature for 15 minutes then treated with 2-aminoethanol (216 mg, 3.5 mmol). The reaction is stirred at room temperature for 18 hours. The reaction is diluted with ethylacetate (75 mL) and washed twice with 1M NaOH (50 mL), dried over magnesium sulfate and concentrated under vacuum. The crude material is purified by silica chromatography using a gradient of 50:50 hexane:ethylacetate to 100% ethylacetate to give the title compound (1.16 g): LCMS (M+H) 410.2.

Step 2: Preparation of 3-(5,5-dimethyl-1,3-dioxan-2-yl)-4-((2R,6R)-2,6-dimethylmorpholino)-5-fluoro-N-(2-oxoethyl)benzamide

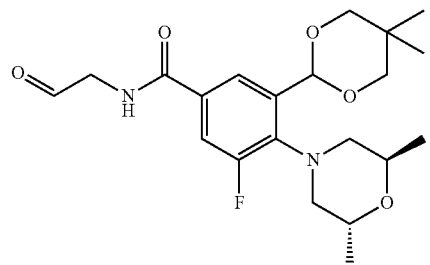

To a solution of the product of Step 1—Example 3 (1.10 g, 2.68 mmol) in dimethylsulfoxide (10 mL) is added 2-iodobenzoic acid (3.30 g, 5.4 mmol). The reaction is stirred at room temperature for 18 hours. The reaction is diluted with ethylacetate (75 mL), washed twice with saturated NaHCO₃ (50 mL), dried and concentrated under vacuum. The crude material is purified using silica chromatography to give the title compound (206 mg): LCMS (M+H) 408.2.

Step 3: Preparation of (2R,6R)-4-(2-(5,5-dimethyl-1,3-dioxan-2-yl)-6-fluoro-4-(oxazol-2-yl)phenyl)-2,6-dimethylmorpholine

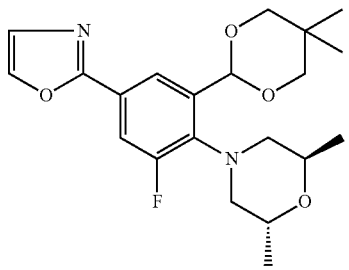 [SMILES: C[C@@H]1CN(c2c(F)cc(-c3ncco3)cc2C2OCC(C)(C)CO2)C[C@@H](C)O1]

Using the same procedure as Step 6—Example 1 but using the product of Step 2—Example 3 and making non-critical variations the title compound is obtained (92 mg): LCMS (M+H) 390.2.

Step 4: Preparation of (2R,4S,4aS)-10-fluoro-2,4-dimethyl-8-(oxazol-2-yl)-2,4,4a,6-tetrahydro-1H,1'H-spiro[[1,4]oxazino[4,3-a]quinoline-5,5'-pyrimidine]-2',4',6'(3'H)-trione

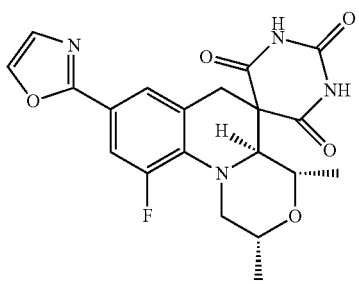

Using the same procedure as Step 7—Example 1 and making non-critical variations the title compound is obtained as a single enantiomer (32 mg): ¹HNMR (400 MHz, DMSO-d₆): 0.87 (d, 3H), 1.08 (d, 3H), 2.91 (d, 1H), 2.98 (m, 1H), 3.54 (d, 1H), 3.61 (m, 1H), 3.72 (m, 1H), 3.84 (d, 1H), 4.05 (d, 1H), 7.25 (d, 1H), 7.38 (s, 1H), 7.46 (d, 1H), 8.07 (d, 1H); LCMS (M+H) 414.1.

Example 4

Preparation of (2R,4S,4aS)-9,10-difluoro-2,4-dimethyl-8-(2-methyloxazol-5-yl)-2,4,4a,6-tetrahydro-1H,1'H-spiro[[1,4]oxazino[4,3-a]quinoline-5,5'-pyrimidine]-2',4',6'(3'H)-trione

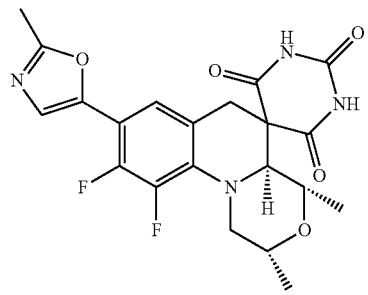

Using the same procedures as Example 1 and making non-critical variations the title compound is obtained as a single enantiomer (320 mg): ¹H NMR (400 MHz, DMSO-d₆) 0.86 (d, 3H), 1.08 (d, 3H), 2.41 (s, 3H), 2.73-2.90 (m, 1H), 2.96-3.05 (m, 1H), 3.50 (d, 1H), 3.55-3.65 (m, 1H), 3.81 (d, 1H), 3.94-4.09 (m, 1H), 7.07 (d, 1H), 7.14 (d, 1H), 11.4 (d, 1H), 11.79 (d, 1H); LCMS (M+H) 446.1.

Example 5

Preparation of (2R,4S,4aS)-9,10-difluoro-2,4-dimethyl-8-(oxazol-4-yl)-2,4,4a,6-tetrahydro-1H,1'H-spiro[[1,4]oxazino[4,3-a]quinoline-5,5'-pyrimidine]-2',4',6'(3'H)-trione

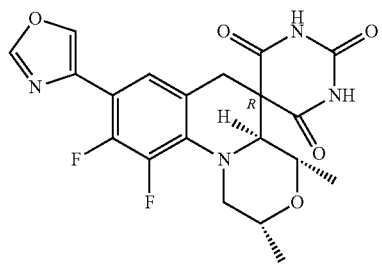

Using the same procedures as Example 7 and making non-critical variations the title compound is obtained as a single enantiomer (193 mg): ¹H NMR (400 MHz, DMSO-d₆) 0.90 (d, 3H), 1.12 (d, 3H), 2.91-2.2.87 (m, 1H), 3.06-3.00 (m, 1H), 3.55 (d, 1H), 3.66-3.62 (m, 1H), 3.77-3.74 (d, 1H), 3.83 (d, 1H), 4.03 (d, 1H), 7.33 (d, 1H), 8.30 (d, 1H), 8.48 (s, 1H), 11.46 (br s, 1H), 11.80 (br s, 1H); LCMS (M+H) 432.1.

Example 6

Preparation of (2R,4S,4aS)-9-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione

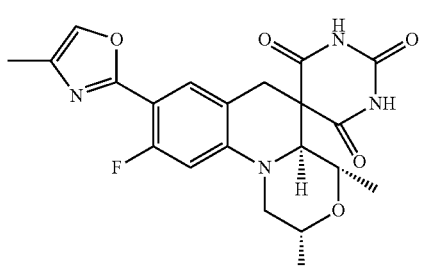

Using the same procedures as Example 3 and making non-critical variations the title compound is obtained as a single enantiomer (320 mg): $^1$H NMR (400 MHz, DMSO-$d_6$) 0.92 (d, 3H), 1.13 (d, 3H), 2.11 (s, 3H), 2.92-2.2.80 (m, 2H), 3.61-3.46 (m, 3H), 3.80 (d, 1H), 4.13 (d, 1H), 6.89 (d, 1H), 7.48 (d, 1H), 7.78 (s, 1H), 11.50 (br s, 1H), 11.80 (br s, 1H); LCMS (M+H) 428.2.

Example 7

Preparation of (2R,4S,4aS)-9,10-difluoro-8-(4-(4-fluorophenyl)oxazol-5-yl)-2,4-dimethyl-2,4,4a,6-tetrahydro-1H,1'H-spiro[[1,4]oxazino[4,3-a]quinoline-5,5'-pyrimidine]-2',4',6'(3'H)-trione

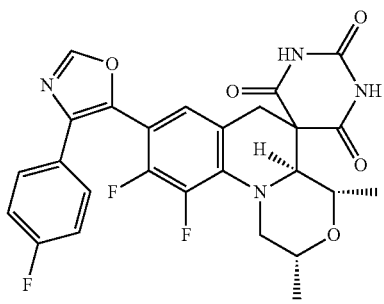

Step 1: Preparation of 4-((2R,6S)-2,6-dimethylmorpholino)-5-(1,3-dioxolan-2-yl)-2,3-difluorobenzaldehyde

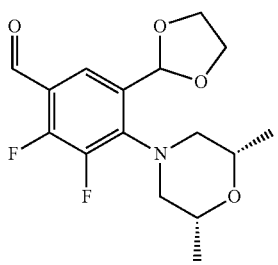 [SMILES: C[C@@H]1CN(c2c(C3OCCO3)cc(C=O)c(F)c2F)C[C@H](C)O1]

To a solution of (2R,6S)-4-(4-bromo-6-(1,3-dioxolan-2-yl)-2,3-difluorophenyl)-2,6-dimethylmorpholine (previously described in WO2004031195, page 81, 0.500 g, 1.32 mmol) and tetramethylethylene-diamine (0.12 mL, 2.12 mmol) in tetrahydrofuran (12 mL) at −78° C. is added t-buthyllithium (1.94 mL, 3.31 mmol). The reaction is stirred at −78° C. for 1.5 h and dimethylformamide is added. The reaction is stirred at −78° C. for an additional 30 min and warmed to rt. Mixture is diluted with ethylacetate (50 mL) and washed with saturated aqueous NH$_4$Cl. (50 ml) and brine (30 mL). Dried over Na$_2$SO$_4$ and concentrated to give the title compound (433 mg): LCMS (M+H) 327.1.

Step 2: Preparation of (2R,6S)-4-(6-(1,3-dioxolan-2-yl)-2,3-difluoro-4-(4-(4-fluorophenyl)oxazol-5-yl)phenyl)-2,6-dimethylmorpholine

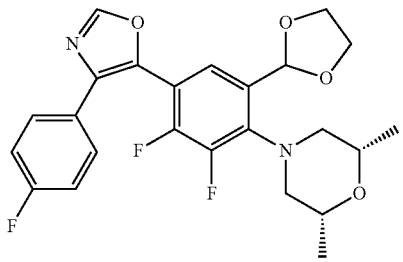 [SMILES: C[C@@H]1CN(c2c(C3OCCO3)cc(-c3ocnc3-c3ccc(F)cc3)c(F)c2F)C[C@H](C)O1]

To a solution of the product of Step 1—Example 7 (0.400 g, 1.22 mmol) in methanol (8 mL) is added sodium methoxide (0.33 g, 6.11 mmol). The solution is stirred for 5 minutes and tosylmethyl isocyanide (0.427 g, 1.47 mmol) is added in portions. The reaction is refluxed for 1 hour, then diluted with water (25 mL) and extracted with CH$_2$Cl$_2$ (3×25 mL). The combined organics are dried over Na$_2$SO$_4$ and concentrated. Purification by chromatography provided the title compound (0.389 g): LCMS (M+H) 460.2.

Step 3: Preparation of (2R,4S,4aS)-9,10-difluoro-8-(4-(4-fluorophenyl)oxazol-5-yl)-2,4-dimethyl-2,4,4a,6-tetrahydro-1H,1'H-spiro[[1,4]oxazino[4,3-a]quinoline-5,5'-pyrimidine]-2',4',6'(3'H)-trione

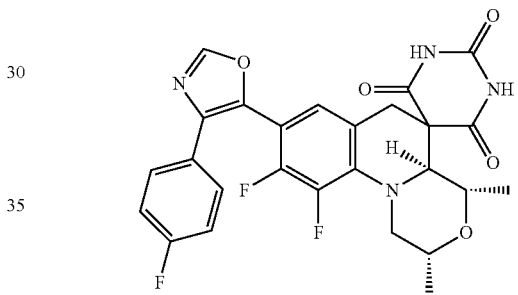

Using the product of Step 2—Example 7, the same procedures as Step 7—Example 1 and making non-critical variations the title compound is obtained as a racemic mixture (290 mg): $^1$H NMR (400 MHz, DMSO-$d_6$) 0.91 (d, 3H), 1.13 (d, 3H), 2.90-2.87 (m, 2H), 3.11-3.06 (m, 1H), 3.48 (d, 1H), 3.70-3.63 (m, 1H), 3.76-3.74 (m, 1H), 3.89 (d, 1H), 4.08 (d, 1H), 6.98 (d, 1H), 7.27-7.23 (m, 2H), 7.56-7.53 (m, 2H), 11.55 (d, 1H), 11.84 (d, 1H); LCMS (M+H) 526.2.

Example 8

Preparation of (2S,4R,4aR)-2,4-dimethyl-8-(oxazol-5-yl)-2,4,4a,6-tetrahydro-1H,1'H-spiro[[1,4]oxazino[4,3-a]quinoline-5,5'-pyrimidine]-2',4',6'(3'H)-trione

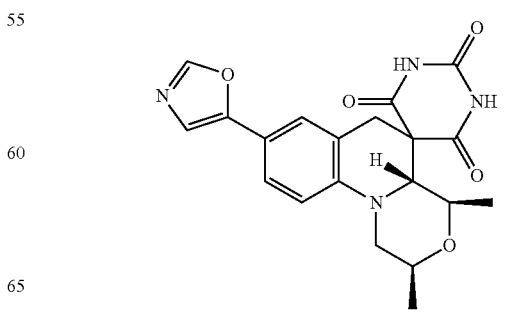

Using the same procedures as Example 7 and making non-critical variations the title compound is obtained as a mixture of diastereoisomers (330 mg): $^1$H NMR (400 MHz, DMSO-$d_6$) 0.92 (d, 3H), 1.15 (d, 3H), 2.95-2.90 (m, 2H), 3.36 (s, 1H), 3.64-3.55 (m, 2H), 3.72 (d, 1H), 4.10 (d, 1H), 6.94 (d, 1H), 7.24 (s, 1H), 7.33 (s, 1H), 7.42 (dd, 1H), 8.28 (s, 1H), 11.45 (s, 1H), 11.77 (s, 1H); LCMS (M+H) 396.1.

Example 9

Preparation of (2S,4R,4aR)-8-(4-ethyloxazol-2-yl)-9,10-difluoro-2,4-dimethyl-2,4,4a,6-tetrahydro-1H,1'H-spiro[[1,4]oxazino[4,3-a]quinoline-5,5'-pyrimidine]-2',4',6'(3'H)-trione

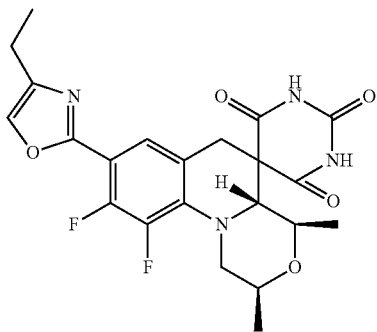

Using the same procedures as Example 7 and making non-critical variations the title compound is obtained as a racemic mixture (30 mg): LCMS (M+H) 461.1.

Example 10

Preparation of (2R,4S,4aS)-9,10-difluoro-2,4-dimethyl-8-(oxazol-2-yl)-2,4,4a,6-tetrahydro-1H,1'H-spiro[[1,4]oxazino[4,3-a]quinoline-5,5'-pyrimidine]-2',4',6'(3'H)-trione

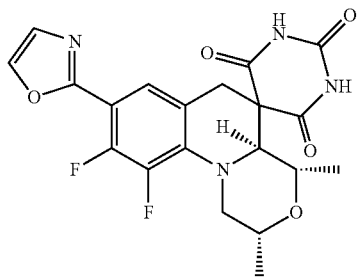

Using the same procedure as Step 7—Example 1 and making non-critical variations the title compound is obtained as a single enantiomer (41 mg): $^1$HNMR (400 MHz, DMSO-$d_6$): 0.91 (d, 3H), 1.13 (d, 3H), 2.89 (d, 1H), 3.07 (t, 1H), 3.66-3.57 (m, 2H), 3.76 (t, 1H), 3.88 (d, 1H), 4.08 (d, 1H), 7.35 (s, 1H), 7.39 (d, 1H), 8.17 (s, 1H), 11.52 (s, 1H), 11.85 (s, 1H); LCMS (M+H) 432.1.

Example 11

In this example, the in vitro antibacterial activity of selected compounds was determined against S. pyogenes 02C0203. Except for clarifying or modifying statements, MIC testing followed procedures recommended by the NCCLS[1-2] or followed the descriptions cited below.

Bacterial Cultures

At least the following organisms are included in the screen: S. pyogenes 02C0203. Incubations were at 35° C. Stock bacterial cultures were maintained on Tryptic Soy Agar containing 5% Sheep Blood (BD, Becton Dickinson Microbiology Systems, Cockeysville, Md.), anaerobes were maintained on Anaerobic Blood Agar plates—CDC Formulation (BD), and fastidious organisms were maintained on Chocolate Agar II Plates (BD). Specific conditions of handling are listed below.

Permanent Stock Culture Collection

Stock cultures are stored as frozen suspensions at −70° C. Most cultures are routinely suspended in 10% skim milk (BD) prior to snap freezing in dry ice/ethanol and then placed in a −70° C. freezer.

Maintenance of Stock Cultures

Most cultures were maintained on Tryptic Soy Agar containing 5% Sheep Blood at room temperature (20° C.). Each culture was recovered from frozen and transferred an additional time before MIC testing. Fresh plates were inoculated the day before testing, incubated overnight, and checked to confirm purity and identity.

Confirming Identity of Cultures

Culture identifications were confirmed by standard microbiological methods[3]. Cultures were streaked onto appropriate agar plates for visualization of purity, expected colony morphology, and hemolytic patterns. Gram stains were also utilized.

The identities of recent isolates used in this test were confirmed using a MicroScan WalkAway 40 SI Instrument (Dade Behring, West Sacramento, Calif.). This device utilizes an automated incubator, reader, and computer to assess for identification purposes the biochemical reactions carried out by each organism. Using this machine, organism identification (confirmation) and an initial antibiogram was generated for each strain.

Standardized Organism Inocula

Frozen stock cultures were used as the initial source of organisms for performing microbroth dilution MIC testing. Stock cultures were passed on their standard growth medium for at least 1 growth cycle (18 to 24 hours) prior to their use.

Most bacteria, unless otherwise noted, were prepared directly from agar plates in 10 mL aliquots of the appropriate broth medium. Bacterial cultures were adjusted to the opacity of a 0.5 McFarland Standard (optical density value of 0.28-0.33 on a Perkin-Elmer Lambda EZ150 Spectrophotometer Wellesley, Mass., set at a wavelength of 600 nm). The adjusted cultures were diluted 400 fold (0.25 mL inoculum+100 mL broth) in growth media to produce a starting suspension of approximately 5×10$^5$ colony forming units (CFU)/mL. Unless otherwise noted, bacterial strains were tested in cation adjusted Mueller Hinton Broth (CAMHB).

Test Compound ("Drug") Preparation

Compounds were solubilized in DMSO. Drug stock solutions were prepared on the day of testing. Drugs were weight corrected for assay content where necessary.

Drug Dilution Tray Preparation

Microbroth dilution stock plates were prepared in two dilution series, 64 to 0.06 μg drug/mL and 0.25 to 0.00025 μg drug/mL. For the high concentration series, 200 μL of stock solution (2 mg/mL) was added to duplicate rows of a 96-well microtiter plate. This was used as the first well in the dilution series. Serial two-fold decremental dilutions were made using a BioMek FX robot (Beckman Coulter Inc., Fullerton, Calif.) with 10 of the remaining 11 wells, each of which contained 100 μL of the appropriate solvent/diluent. Row 12 contained solvent/diluent only and served as the control. For tube one of the low concentration series, 200 μL of an 8 μg/mL stock was added to duplicate rows of a 96-well plate. Serial two-fold dilutions were made as described above.

Daughter plates were spotted (3.2 μL/well) from the stock plates listed above using the BioMek FX robot and were either used immediately or frozen at −70° C. until use.

broth tray. The MIC was the lowest concentration of drug that prevented macroscopically visible growth under the conditions of the test. Testing was performed in duplicate. When the MIC values in duplicate tests varied by 1 well (2-fold), the lower values were reported. If the MICs varied by 2 dilutions, the middle value was reported. Greater than this 4-fold variance called for the test to be repeated, after which a similar determination was applied to all values.

TABLE 1

MICs against *S. pyogenes* 02C0203

| Compound | Structure | S. pyogenes 02C0203 MIC (μg/mL) |
| --- | --- | --- |
| Example 1 | 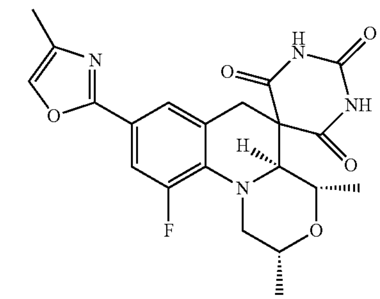 | 1 |
| Example 9 | 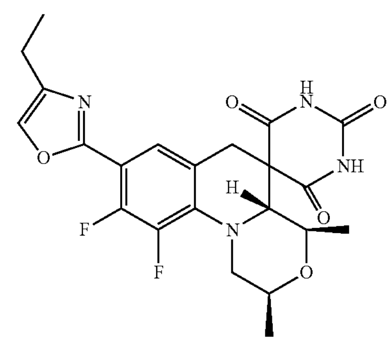 | 1 |
| Comparator Compound from the Literature | 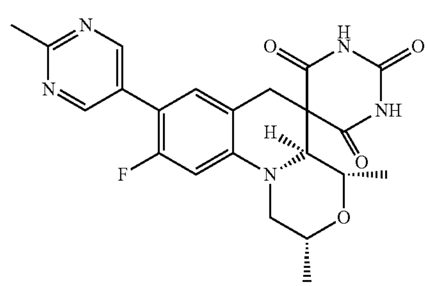 | 2 |

Plate Inoculation

Aerobic organisms were inoculated (100 μL volumes) into the thawed plates using the BioMek FX robot. The inoculated plates were placed in stacks of no more than 5 and covered with an empty plate. These plates were incubated 16 to 24 hours in ambient atmosphere according to CLSI guidelines[2].

Reading the Test

After inoculation and incubation, the degree of bacterial growth was estimated visually with the aid of a Test Reading Mirror (Dynex Technologies 220 16) in a darkened room with a single light shining directly through the top of the micro- Example 11 demonstrates the antibacterial activity of the compounds of Examples 1 and 9 of the present invention.

Example 12

In this example, the plasma concentrations of selected compounds were determined in mice that were infected with *S. pyogenes* 02C0203 at an oral dose of 100 mg/kg[4]. Plasma samples were assayed for selected compounds using LC/MS/MS with multiple reaction monitoring. Free fractions were measured using equilibrium dialysis[5].

TABLE 2

Mean plasma concentrations vs. time of compounds in mice (n = 3) that were infected with *S. pyogenes* 02C0203 at a dose of 100 mg/kg[4]

| Time (hours) | Mean plasma concentration of Example 1 (ng/mL) | Mean plasma concentration of Example 9 (ng/mL) | Mean plasma concentration of Comparator Compound (ng/mL) |
|---|---|---|---|
| 0.5 | 13500 | 19400 | 11100 |
| 1 | 13300 | 19000 | 17100 |
| 2 | 21500 | 23000 | 16000 |
| 4 | 24500 | 22900 | 8530 |
| 8 | 7450 | 18100 | 3700 |
| 24 | 176 | 2180 | 1400 |

In Example 12, the compounds of Examples 1 and 9 of the present invention have demonstrated oral exposure, such as in mice infected with *S. pyogenes* 02C0203 at a dose of 100 mg/kg[4].

Example 13

In this example, the in vivo antibacterial efficacy of selected compounds was determined in a neutropenic soft tissue infection model in CF-1 female mice challenged with *Streptococcus pyogenes* 02C0203. With the exception of modifications discussed here, the murine soft tissue infection model was previously described by Craig et al. (6, 7, 8).

CF-1 female mice were immunosuppressed with oral doses of cyclophosphamide in sterile water on Day-4 (150 mg/kg) and Day-1 (100 mg/kg). Mice were infected intramuscularly (thigh muscle) with 7×10[5] cfu of *S. pyogenes* 02C0203 in 0.1 ml brain heart infusion broth on Day 0. Two hours post-infection, mice received a single oral dose of selected compounds. The compounds were administered orally from a spray dried dispersion (SDD) in 0.5% (wt/v) methylcellulose (MC), 0.5% (wt/v) hydroxypropyl methylcellulose acetate succinate medium, fine powder (HPMCAS-MF) in 20 mM Tris buffer (pH 7.4). Thigh tissue was collected 24 hours post-dose. Serial ten-fold dilutions of tissue homogenates prepared in sterile phosphate buffered saline were plated on 5% sheep blood agar plates for enumeration of bacterial burden.

Separate groups of immunosuppressed mice were infected as above and orally dosed 2 hours post-infection with 100 mg/kg of the selected compounds. Thigh tissue samples (10% in PBS) and plasma were collected at 0.5, 1, 2, 4, 8 and 24 hours post-dose (n=3) for quantitation of drug levels. Bacterial burden was quantitated in the thigh tissue samples from treated mice and from infected, untreated mice at each timepoint.

TABLE 3

In vivo efficacy of selected compounds in the neutropenic thigh abscess infection model caused by *S. pyogenes* 02C0203

| Compound | Dose (mg/kg) | $\text{Log}_{10}$ geometric mean recoverable cfu | Mean $\log_{10}$ cfu reduction vs. infected controls |
|---|---|---|---|
| Example 1 | 200 | 2.85 | 3.85 |
| Example 1 | 100 | 3.49 | 3.21 |
| Example 1 | 50 | 4.60 | 2.10 |
| Example 1 | 25 | 5.45 | 1.25 |
| Example 1 | 12.5 | 6.17 | 0.53 |
| Example 2 | 200 | 1.92 | 4.78 |
| Example 2 | 100 | 2.11 | 4.59 |
| Example 2 | 50 | 5.07 | 1.63 |
| Example 2 | 25 | 5.76 | 0.94 |
| Example 2 | 12.5 | 6.23 | 0.47 |
| Comparator Cpd | 200 | 4.32 | −2.27 |
| Comparator Cpd | 100 | 4.62 | −1.97 |
| Comparator Cpd | 50 | 6.48 | −0.11 |
| Comparator Cpd | 25 | 6.52 | −0.07 |
| Comparator Cpd | 12.5 | 6.48 | −0.11 |
| Untreated control | | 6.70 | — |

TABLE 4

AUC/MIC ratios required for efficacy agains *S. pyogenes* 02C0203 for selected compounds.

| Compound | Target fAUC (µg * hours/mL) | *S. pyogenes* 02C0203 MIC (µg/mL) | fAUC |
|---|---|---|---|
| Example 1 | 2 | 1 | 2 |
| Example 9 | 4 | 1 | 4 |

Based on the MIC values, mouse exposure and exposure required for efficacy, as demonstrated by the results obtained in Examples 11-13, the compounds of Examples 1 and 9 of the present invention have lower dose projections than the comparator compound due to lower AUC/MIC ratios (as shown in Table 4), which are required to meet PK-PD endpoints for antibacterial activity, such as against *S. pyogenes* 02C0203.[5,6]

What is claimed is:
1. A compound selected from the group consisting of:
 (2R,4S,4aS)-10-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-9,10-difluoro-2,4-dimethyl-8-(3-methyl-isoxazol-5-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-10-fluoro-2,4-dimethyl-8-(oxazol-2-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-9,10-difluoro-2,4-dimethyl-8-(2-methyloxazol-5-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-9,10-difluoro-2,4-dimethyl-8-(oxazol-4-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-9-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione;
 (2R,4S,4aS)-9,10-difluoro-8-(4-(4-fluorophenyl)oxazol-5-yl)-2,4-dimethyl-2,4,4a,6-tetrahydro-1H,1'H-spiro[[1,4]oxazino[4,3-a]quinoline-5,5'-pyrimidine]-2',4',6'(3'H)-trione;
 (2S,4R,4aR)-2,4-dimethyl-8-(oxazol-5-yl)-2,4,4a,6-tetrahydro-1H,1'H-spiro[[1,4]oxazino[4,3-a]quinoline-5,5'-pyrimidine]-2',4',6'(3'H)-trione;

(2S,4R,4aR)-8-(4-ethyloxazol-2-yl)-9,10-difluoro-2,4-dimethyl-2,4,4a,6-tetrahydro-1H,1'H-spiro[[1,4]oxazino[4,3-a]quinoline-5,5'-pyrimidine]-2',4',6'(3'H)-trione; and (2R,4S,4aS)-9,10-difluoro-2,4-dimethyl-8-(oxazol-2-yl)-2,4,4a,6-tetrahydro-1H,1'H-spiro[[1,4]oxazino[4,3-a]quinoline-5,5'-pyrimidine]-2',4',6'(3'H)-trione;

or an enantiomer or diastereomer thereof or a pharmaceutically acceptable salt, solvate, or hydrate thereof.

2. A compound of claim 1 wherein the compound is (2R,4S,4aS)-10-fluoro-2,4-dimethyl-8-(4-methyloxazol-2-yl)-2,4,4a,6-tetrahydro-1H,1'H-spiro[[1,4]oxazin[4,3-a]quinoline-5,5'-pyrimidine]-2',4',6'(3'H)-trione or an enantiomer or diastereomer or a pharmaceutically acceptable salt, solvate or hydrate thereof.

3. A compound of claim 2 wherein the compound is (2R,4S,4aS)-10-fluoro-2,4-dimethyl-8-(4-methyloxazol-2-yl)-2,4,4a,6-tetrahydro-1H,1'H-spiro[[1,4]oxazino[4,3-a]quinoline-5,5'-pyrimidine]-2',4',6'(3'H)-trione.

* * * * *